United States Patent
Coty et al.

[11] Patent Number: 5,961,553
[45] Date of Patent: Oct. 5, 1999

[54] LONG BONE ELONGATION DEVICE

[75] Inventors: Alain Coty, Sagy; Emmanuel Favreul, Strasbourg; Michel L'Homme, Rueil Malmaison, all of France; Giovani Peretti, Milan, Italy; Dror Palay, Baltimore, Md.

[73] Assignee: Medinov-Amp, Roanne, France

[21] Appl. No.: 08/894,137

[22] PCT Filed: Jan. 15, 1996

[86] PCT No.: PCT/FR96/00065

§ 371 Date: Jan. 26, 1998

§ 102(e) Date: Jan. 26, 1998

[87] PCT Pub. No.: WO96/25117

PCT Pub. Date: Aug. 22, 1996

[30] Foreign Application Priority Data

Feb. 13, 1995 [FR] France .................. 95 01 628

[51] Int. Cl.⁶ .................................................. A61F 2/28
[52] U.S. Cl. .................................. 623/16; 606/62
[58] Field of Search .............. 623/16, 22; 606/62, 606/105

[56] References Cited

U.S. PATENT DOCUMENTS

| 4,173,796 | 11/1979 | Jarvik . | |
|---|---|---|---|
| 5,156,605 | 10/1992 | Pursley et al. . | |
| 5,415,660 | 5/1995 | Campbell | 606/62 |
| 5,429,638 | 7/1995 | Muschler | 606/62 |
| 5,505,733 | 4/1996 | Justin | 606/62 |
| 5,626,579 | 5/1997 | Muschler | 606/62 |
| 5,626,581 | 5/1997 | Staehlin | 606/62 |
| 5,704,938 | 1/1998 | Staehlin | 606/62 |

FOREIGN PATENT DOCUMENTS

| 2267080 | 11/1975 | France . |
|---|---|---|
| 89 07 561 | 1/1990 | Germany . |

OTHER PUBLICATIONS by K. Koshiji et al., "Externally–Coupled Transcutaneous Energy Transmission System for a Totally Implantable Artificial Heart", *Proceedings of the Annual International Conference of the IEEE Engineering in Medicine and Biology Society*, vol. 15, Oct. 1993, pp. 909–910.

*Primary Examiner*—Michael J. Milano
*Attorney, Agent, or Firm*—Young & Thompson

[57] ABSTRACT

A device for elongating long bones such as thigh bones, shin bones and arm bones, including an intramedullary nail with a tubular sleeve (4), and an extension (5) axially slidable within the sleeve (4). The sleeve and the extension include means (6; 7) for rigidly connecting them to two bone portions separated by an osteotomy, and means for moving the extension (5) relative to the sleeve (4), whereby both the intramedullary nail and the corresponding bone may gradually be elongated. The means for moving the extension (5) relative to the sleeve (4) include an electric motor (8) arranged within the sleeve (4) and linked to a speed reducer (9) driving a screw/nut assembly (13, 14, 15) for moving the extension (5) relative to the sleeve, and means (2) for supplying power to the electric motor (8) and automatically controlling the value and direction of the movement imparted to the extension (5) in the sleeve (4) by the screw/nut assembly (13, 14, 15) driven by the electric motor (8).

10 Claims, 4 Drawing Sheets

LONG BONE ELONGATION DEVICE

The present invention concerns the devices used for elongating long bones such as the femur, tibia and humerus, and it relates more particularly to a device for progressive control of one such elongation device.

Femoral bones of unequal length and cases of dwarfism are presently treated using purely mechanical bone elongation devices.

Although these are satisfactory in terms of the function required of them, these devices, which are called external fixators, restrict the patient and are associated with a very high rate of complications.

Devices for elongating long bones are also known which comprise an intramedullary nail which includes a tubular sleeve, an extension which can slide axially inside the sleeve, the sleeve and the extension being equipped with members for rigidly connecting them to two bone portions separated by an osteotomy, and means for moving the extension in the sleeve, capable of imparting to the intramedullary nail, and to the bone in which it is fixed, a gradual elongation which is obtained automatically or by an external action, the said system being entirely enclosed within the body and the bone in question.

Such a nail, described in European Patent Application No. 0 346 247, filed May 22, 1989 by the Applicant, is made up of several elements which are capable of imparting to the nail a gradual elongation, resulting from a partial rotation applied to the limb in question and a return to the original position.

An elongation device for long bones is also known which comprises an intramedullary nail which includes a tubular sleeve, an extension which can slide axially inside the sleeve, the sleeve and the extension being equipped with members for rigidly connecting them to two portions of the fractured bone, and means for moving the extension in the sleeve, these means of movement comprising a wire which is made of a shape-memory alloy and is arranged axially in the sleeve between one end of the latter and one end of the extension to which the contiguous end part of the wire is fixed, mechanical means for transforming the compressive force, which is produced by the shape-memory wire under the action of successive cycles of heating and cooling of the said wire, into an axial force of distraction exerted on the extension and tending to bring it partially out of the sleeve, means for induction heating of the shape-memory wire, and a generator of heat energy by induction which is provided with a transmitting antenna intended to surround the patient's limb in which the bone is equipped with the intramedullary nail, and designed to cyclically activate the means of heating the shape-memory wire in order to initiate gradual forward movements of the extension so as to bring about an elongation of the nail and consequently an elongation of the bone.

Such an intramedullary nail, described in European Patent Application No. 0 346 247, makes it possible to obtain an elongation, for a long bone such as the femur, of up to 10 cm, and it avoids the problems of sepsis occasioned by the use of an elongation device with external control, as well as the risks of angular deviation during elongation by virtue of the intramedullary guiding.

This elongation nail also permits the formation of a bone callus, followed by a consolidation of lamellar bone which is of substantially better quality than that obtained by the external fixators, and in theory it requires only two operations, one—for its implantation and the other for its removal.

Moreover, it limits the number of scars and in particular limits their size, which represents an important psychological benefit for the patient.

Finally, this type of internal fixator allows the patient to remain active without handicap during the second half of the duration of treatment and avoids the aesthetic problems.

On the other hand, the callus (or osteon) which is formed between the two halves of the bone, and which joins them together, is necessarily broken by the repeated 15° rotations of the leg (30 times a day) in order to obtain a daily elongation of 2 mm, and this tends to cause the patient intense pain. Moreover, the nail lacks linear strength of elongation because of its very small dimensions, and this limits the maximum possible elongation.

The device for elongation of long bones using a wire made of shape-memory alloy described in French Patent Application No. 94 13 244, filed Nov. 4, 1994 in the name of the Applicant, no longer requires the use of repeated rotations of the leg, with the result that the disadvantages caused by the successive ruptures of the callus are eliminated.

However, this latter device, like the one which is described in European Patent Application No. 0 346 247, has the disadvantage that it is not possible to ascertain at any given moment the value of the mechanical action exerted on the intramedullary nail and, for this reason, on the two portions of the limb which is to be elongated, and this makes it very difficult to monitor with precision the elongation procedure, which generally proceeds over a period of the order of three to ten months.

The object of the invention is to remedy this disadvantage by making available a medullary elongation system with which it is possible, on the one hand, to ensure very precise elongation paths, and, on the other hand, to monitor the elongation permanently.

The subject of the invention is therefore an elongation device for long bones, comprising an intramedullary nail which includes a tubular sleeve, an extension which can slide axially inside the sleeve, the sleeve and the extension comprising means allowing them to be rigidly connected to two bone portions separated by an osteotomy, and means for moving the extension relative to the sleeve and capable of imparting to the intramedullary nail, and also to the bone intended to receive it, a gradual elongation, the means for moving the extension relative to the sleeve comprising an electric motor which is arranged in the sleeve and is linked to a speed reducer for driving a screw/nut assembly for moving the extension relative to the sleeve, and means for supplying power to the electric motor and for automatically controlling the value and direction of the movement imparted to the extension in the sleeve by the screw/nut assembly driven by the electric motor, the said power supply and control means including a transformer which comprises a first part intended to be implanted beneath the patient's skin and a second part intended to be applied upon the patient's skin in line with the first part, wherein the first part of the transformer includes a magnetic circuit having, on two end branches, secondary windings for supplying power to the electric motor in two opposite directions, and, on an intermediate branch, a primary winding for receiving signals of the position of the screw of the screw/nut assembly, which signals come from a position sensor driven by the reducer, while the second part of the transformer intended to be arranged in line with the first part by being applied against the patient's skin includes a magnetic circuit having, on two end branches, primary windings connected to a supply circuit and intended to cooperate with the secondary windings of the first part and, on an intermediate branch, a secondary winding intended to cooperate with the primary winding of the first part in order to transmit the position signals of the screw/nut assembly to a filtering and shaping circuit.

The invention will be better understood upon reading the following description which is given solely by way of example and in which reference is made to the attached drawings, in which.

Figure 6:
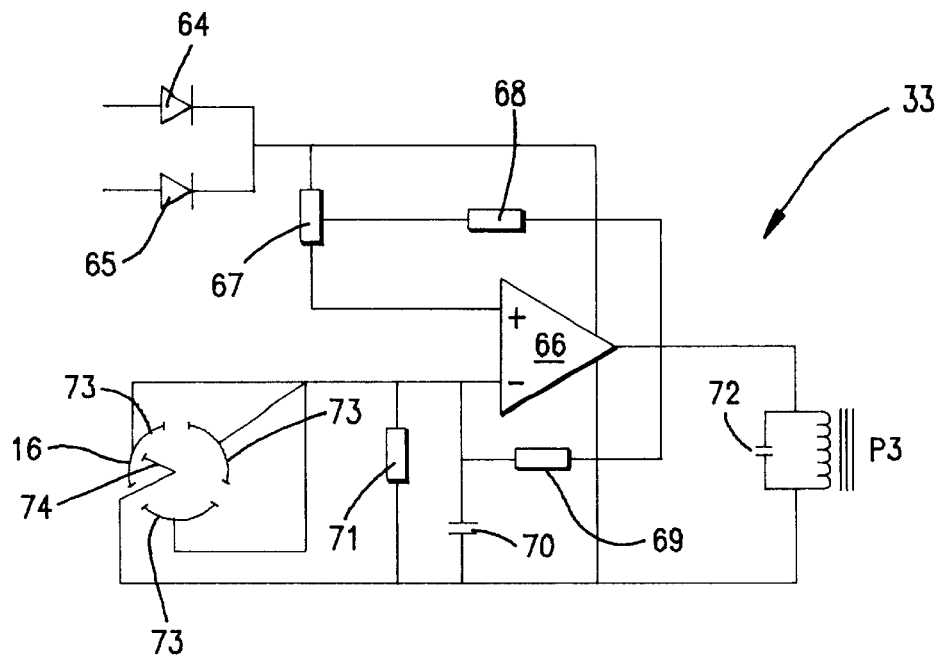
Figure 7:
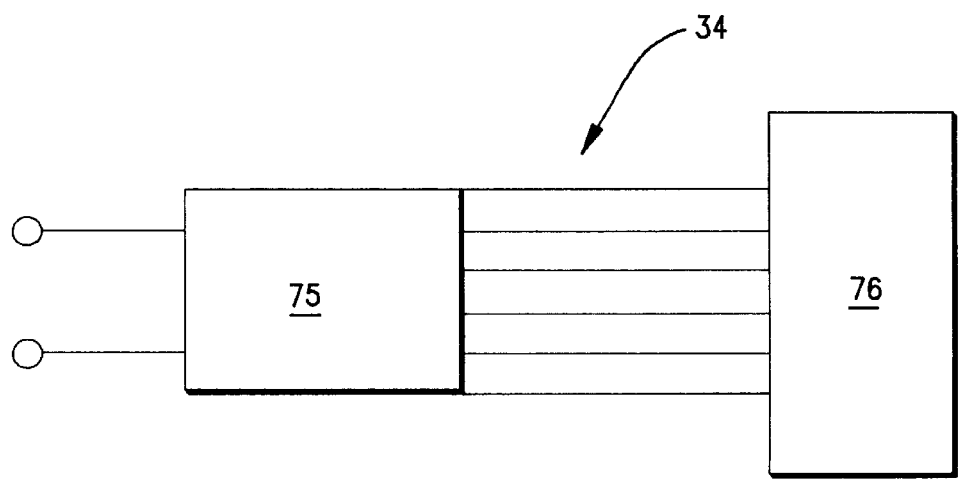

FIG. 6 is an electrical flow chart representing the circuit for transmitting the counting pulses of the elongation steps to the primary winding of the transformer for transmission of data which forms part of the device according to the invention; and FIG. 7 is a block diagram of the means for counting and displaying the signals relating to the state of elongation of the intramedullary elongation device according to the invention.

Figure 1:
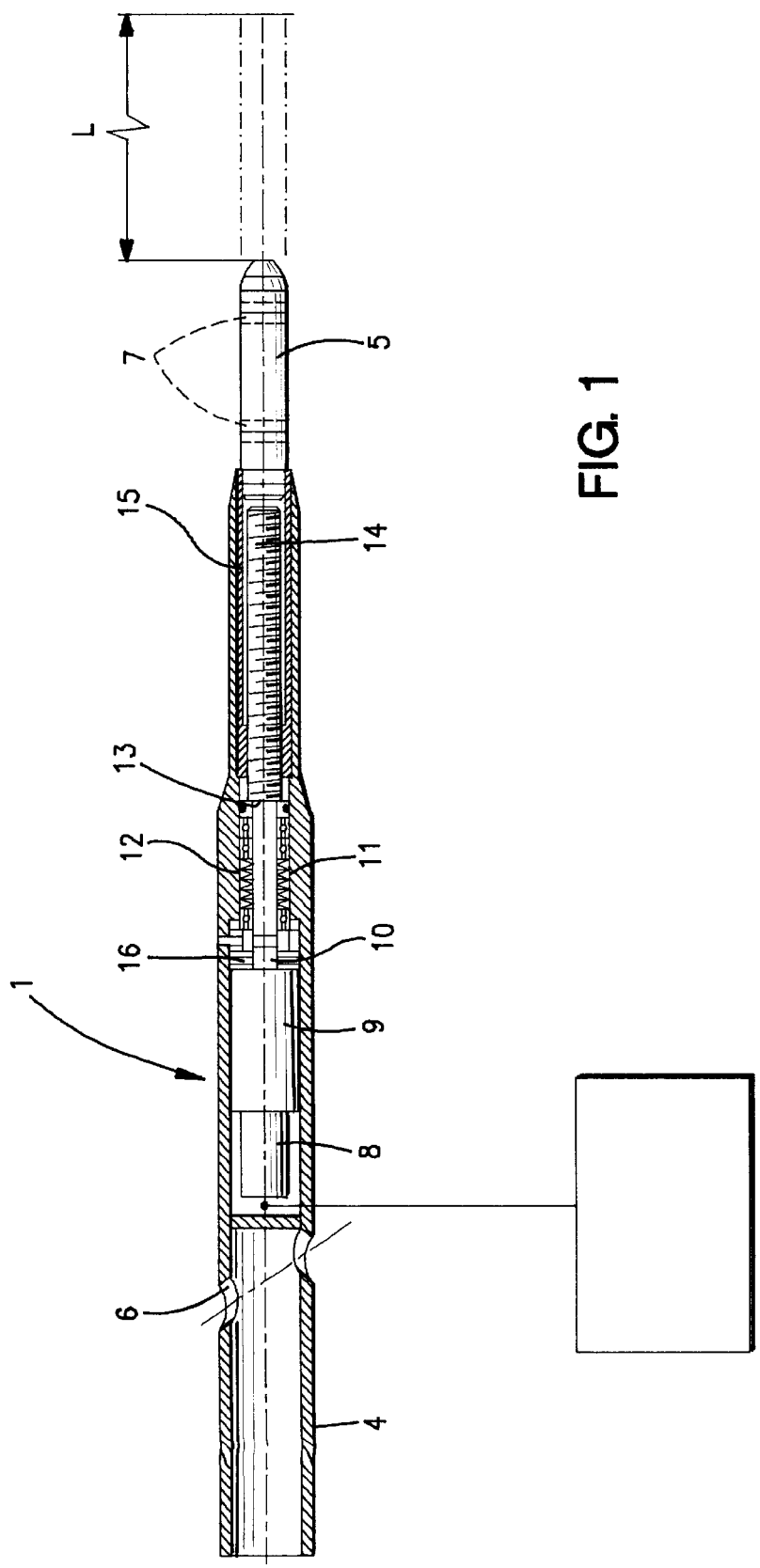
FIG. 1 is a partially cutaway view of a device for gradual intramedullary elongation, motorized in accordance with the invention.

The intramedullary elongation device according to the invention, as represented diagrammatically in FIG. 1, includes an intramedullary nail 1 intended to be placed in the medullary canal of a long bone, such as a femur, which is to be elongated, and an electronic circuit 2 for controlling this device.

The intramedullary nail 1 comprises a tubular sleeve 4 and an extension 5 capable of sliding axially inside the sleeve, the sleeve and the extension being equipped with respective transverse holes 6 and 7 for receiving screws or pins, not shown, intended to be fixed in corresponding portions of the bone to be elongated, in order to immobilize, relative to these portions of the bone, the sleeve 4 on the one hand and the extension 5 on the other, by means of that part of this extension outside the sleeve 4 being fixed to the bone.

Arranged in the sleeve 4 is an electric drive motor 8 which is powered electrically and is controlled by the electronic circuit 2 in a manner which will be described hereinafter.

The electric motor 8 is coupled to a speed reducer 9 whose output shaft 10 is connected, by way of an axial damping device 11 formed by a stack of elastic washers 12, to a rod 13 including a threaded portion 14 which cooperates with a skirt 15 forming a nut which prolongs the extension 5 inside the sleeve 4.

The electric motor 8 is advantageously formed with a diameter of 7.5 mm, whilst the speed reducer also has a very small diameter of the order of 8 mm, for example, and its speed reducing ratio is 8,200, for example.

The rod 13 with threaded portion 14 at the same time drives an incremental sensor 16 which in the present example delivers three pulses per rotation.

The information issuing from the incremental sensor, after being re-transmitted through the skin of a limb equipped with the device according to the invention, makes it possible to quantify the movement of the extension relative to the sleeve, the total travel L of which extension is represented in FIG. 1.

It will be seen that the assembly consisting of the motor 8 and the reducer 9 is highly miniaturized, which allows it to be implanted in the intramedullary elongation device according to the invention.

Figure 2:
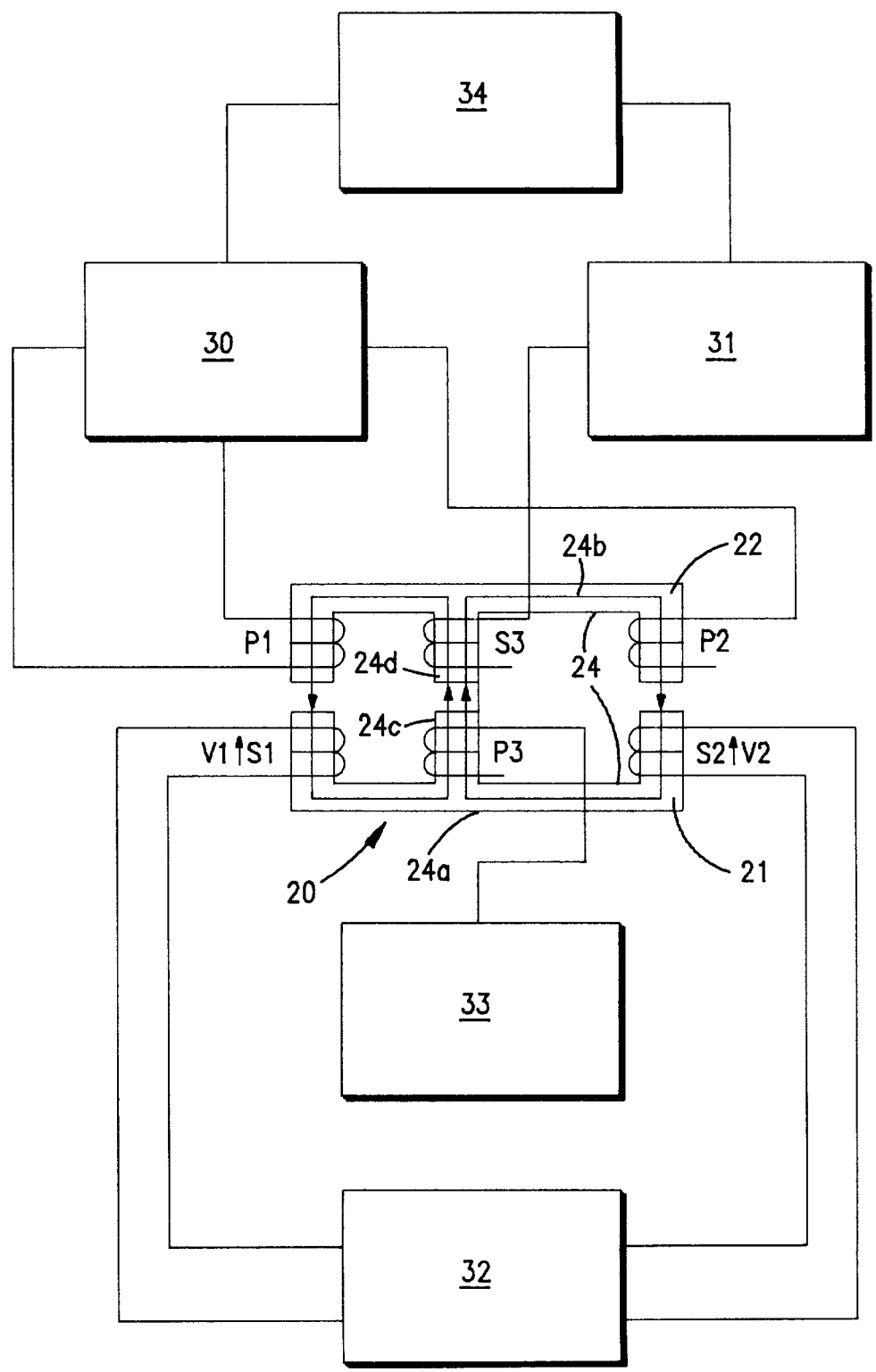
FIG. 2 is a block diagram of the electronic control circuit which forms part of the device in FIG. 1.

Referring to FIG. 2, it will be seen that the electric control circuit of the device according to the invention principally includes a transformer 20 to which various circuits are connected in a manner which will be described hereinafter.

Since introducing a battery into the body poses safety problems, it appeared preferable to use a device which permits the electric energy to be transmitted through a patient's skin.

The power levels used being low and the output criteria without great significance, the Applicant has shown that it is possible to use a transformer with large air gap.

The transformer 20 is thus physically divided into two parts.

It includes a first part 21 implanted beneath the patient's skin and a second part 22 intended to be applied upon the patient's skin in line with the first part 21 whenever it is desired to initiate a movement of the elongation system.

The functions to be realized by the device according to the invention are various, since it is not only necessary to transmit energy from outside to inside the patient's body, but also to be able to receive information concerning the value of the movement of the extension 5 of the intramedullary nail relative to its sleeve 4.

These functions are obtained by linking suitable electronic circuits to the first and second parts 21 and 22 of the transformer 20, which circuits will be described in detail with reference to FIGS. 3 to 7.

The transformer 20 represented in FIG. 2 includes, like any transformer, a magnetic circuit 24 on which windings are arranged.

Primary windings P1, P2 are mounted on end branches of the magnetic circuit 24a of the second part 22 of the transformer and are intended to cooperate with the corresponding secondary windings S1, S2 mounted on end branches of the magnetic circuit 24b of the first part 21 of the transformer in order to transmit the electrical energy from outside the skin towards the electric motor 8.

Concerning the electronic devices which will be described hereinafter, when the primary winding P1 is powered, a voltage V1 is induced in the secondary winding S1 and the motor 8 incorporated in the intramedullary nail turns in a defined direction.

Conversely, when the primary winding P2 is powered, a voltage V2 appears at the terminals of the secondary winding S2 and the motor 8 turns in the opposite direction.

The transformer represented in FIG. 2 additionally includes a primary winding P3 mounted on an intermediate branch 24c of the magnetic circuit 24a of the first part 21 and cooperating with a secondary winding S3 mounted on an intermediate branch 24d of the magnetic circuit 24b of the second part 22 of the transformer.

The winding P3 receives pulse trains each time the position sensor 16 executes a third of a rotation, and these pulses are sensed by the secondary S3 in order to be shaped before counting, in a manner which will be described hereinafter.

It will also be seen in FIG. 2 that the magnetic circuit 24 formed by the first and second parts 24a and 24b is asymmetrical in the sense that the intermediate branches 24c and 24d of its two parts 24a, 24b are arranged at unequal distances from the two corresponding end branches, in such a way as to rule out any uncertainty regarding the direction of rotation of the motor.

This arrangement ensures there can be no confusion of the position of the poles of the first part 21 relative to those of the second part 22 of the transformer 20. The principal function of the second part 22 of the transformer consists in delivering energy to the first part 21. Now, looking at FIG. 2, if we consider the route taken by the flux principally in one branch, it will be noted that some of this flux is diverted to the other branch.

The voltage V1 induced in the secondary S1 by the principal flux tends to turn the motor 8 in one direction.

The voltage V2 induced in the secondary S2 tends, by contrast, to turn the motor 8 in the other direction and consequently to brake it.

In order to avoid these disadvantages, it suffices to power the winding P2 with the exact current value needed to create a compensation flux which annuls the voltage V2.

An identical argument can be made when it is the winding P2 which is to be powered. In this case, it is at the same time necessary to compensate the diverted flux by causing a compensation current of suitable value to circulate in the primary winding P1.

To this end, the circuit in FIG. 2 additionally includes an electronic circuit 30 for powering the primary windings P1 and P2 of the second part 22 of the transformer 20.

A circuit 31 for filtering the output signals from the secondary S3 of the said second part is also provided. The secondary windings S1 and S2 of the first part 21 are connected to the terminals of a circuit 32 for determining the direction of rotation of the motor 8 of the intramedullary nail, whilst the primary P3 of the first part 21 of the transformer is connected to the output of a circuit 33 for generating step signals corresponding to the signals delivered by the position sensor 16 of the device in FIG. 1.

Finally, the circuits 30 and 31 are connected to a circuit 34 for counting and displaying the signals relating to the state of elongation of the intramedullary elongation device according to the invention.

Figure 3:
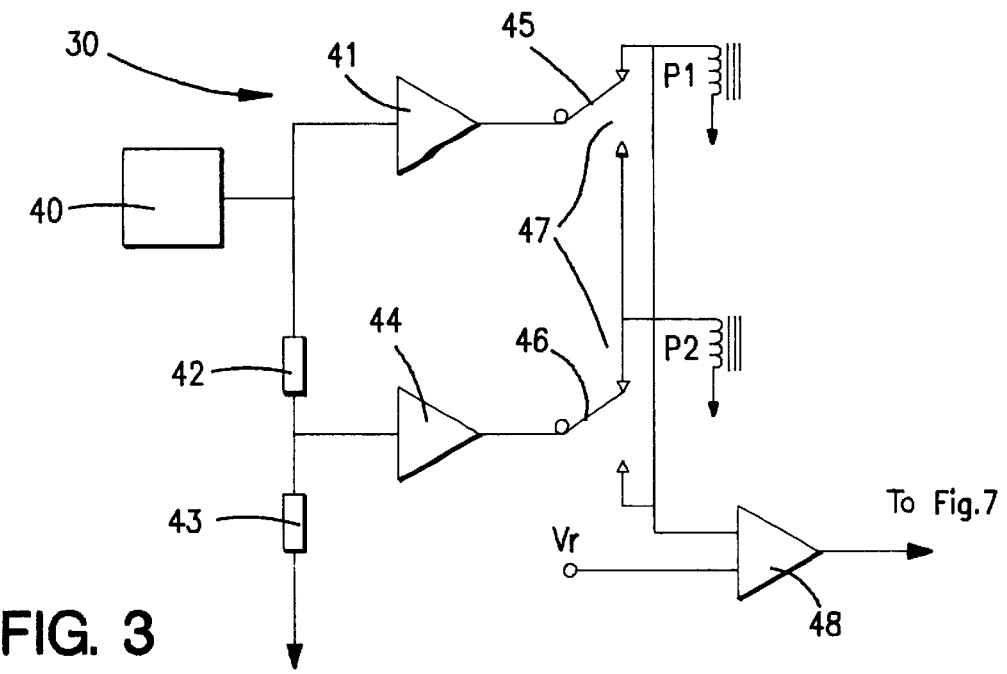
FIG. 3 shows an electronic flow chart for the power supply circuit of the primary of the transformer which forms part of the control device in FIG. 2.

The circuit 30 for powering the primaries P1 and P2 of the transformer represented in detail in FIG. 3 includes principally an oscillator 40 having a frequency of the order of 10,000 Hz, the output of which is connected directly to the input of a first amplifier 41 and, by way of a voltage divider made lip of two resistors 42, 43, to the input of a second amplifier 44.

Thus, the amplifier 41 is the principal power amplifier, whereas the amplifier 44 is a compensation amplifier.

The outputs of the amplifiers 41 and 44 are connected to respective coupled mobile contacts 45, 46 of a two-way inverter 47. A fixed contact associated with the mobile contact 45 is connected to a first terminal of the primary winding P1, whilst its other fixed contact is connected to a first terminal of the primary winding P2. One of the fixed contacts linked to the mobile contact 46 is also itself connected to the first terminal of the winding P2, while its other fixed contact is connected to the first terminal of the winding P1.

The first terminal of the primary winding P1 is additionally connected to an input of a differential amplifier 48 whose other input is connected to a reference voltage Vr. The other terminals of the primary windings P1 and P2 are earthed, in the same way that the resistor 43 of the voltage divider 42, 43 is also earthed.

The oscillator 40 either powers the principal power amplifier 41 directly, or powers the compensation amplifier 44 by way of the divider bridge 42, 43. The role of this voltage divider is to precisely adjust the compensation flux.

To choose the direction of rotation of the motor 8, it suffices to actuate the switch 47 in such a way as to direct the principal current towards one or other of the two primary windings P1 or P2, the primary winding which is connected to the principal power amplifier 41 determining the direction of rotation of the motor, whilst the primary winding connected to the compensation amplifier 44 receives a compensation current of a direction and strength appropriate to compensate the diverted flux which runs through it on account of the other primary winding being powered by the principal power amplifier.

As has been explained hereinabove, by virtue of an incremental sensor, such as the sensor 16 borne by the output shaft of the reducer 9 of the intramedullary elongation device represented in FIG. 1, it is possible to count the number of rotations executed by the threaded rod 13, 14 and thereby to know the value of the translational movement of the extension 5 relative to the sleeve 4.

However, to carry out such an evaluation, the direction in which the threaded rod 13, 14 is rotated needs to be known. This information is obtained by virtue of the presence of the comparator 48 whose function consists in determining which of the primary windings P1 or P2 is receiving the main energizing current originating from the oscillator 40, and in delivering a corresponding logic signal.

To this end, the comparator 48 delivers an output signal with two states 0 or 1 after comparison of the signal which it receives at its input connected either to the primary winding P1 or to the primary winding P2 depending on the position of the mobile contacts 45, 46 of the inverter 47, with the reference voltage Vr applied to its other input.

To ensure that the counting pulses are easily discriminated, the frequency of their carrier wave needs to be very different from that used to transfer the energy.

The frequency of the supply oscillator 40 having been chosen equal to 10 kHz, the frequency of the carrier wave of the counting signals is advantageously chosen equal to 170 kHz. The carrier wave of the counting signals is generated by the circuit 33 which will be described in detail with reference to FIG. 6 and is applied to the primary winding P3 of the first part 21 of the transformer 20.

The signals received by the primary winding P3 are transmitted to the secondary winding S3 of the second part 22 of the transformer external to the body of the patient and are applied to the circuit 31 which will now be described with reference to FIG. 4.

This circuit includes, connected to the secondary winding S3, a filter 50 for the voltage induced at the terminals of a winding S3 which extracts the desired information and whose output is in turn connected, by way of a detector 51, to a shaping circuit 52 intended to convert detected signals into square signals and connected, as is represented in FIG. 2, to a counting input of the circuit 34 which will be described with reference to FIG. 7.

The simple fact that the transformer represented in FIG. 2 includes two separate secondary windings S1 and S2, which can when necessary become voltage generators, is not sufficient to correctly power the motor 8 in one or other of the two directions of rotation.

It is further necessary that the rectifier circuit linked to each of these secondary windings delivers uniquely to the motor 8 and is therefore controlled by the supply voltage itself.

To satisfy this condition, the Applicant has conceived an electronic circuit which constitutes a sort of automaticcontrol bridge rectifier. Such an arrangement designated by general reference 32 in FIG. 2 will be described in detail with reference to FIG. 5.

It will be seen in this figure that the secondary winding S1 of the transformer 20 is connected in series to a diode 54 and two resistors 55, 56 forming a voltage divider. The base of a transistor 57 is connected to the junction point of the resistors 55 and 56, the emitter-collector path of which transistor 57 is connected to a terminal of the electric motor 8. The diode 54 is additionally connected to the other terminal of the electric motor 8.

The secondary winding S2 is similarly connected in series with a diode 58 and two resistors 59, 60 forming a voltage divider. The base of another transistor 61 is connected to the junction point of the resistors 59 and 60, the emitter-collector path of which transistor 61 is connected to the said other terminal of the motor 8. The diode 58 is also connected to the terminal of the electric motor 8 linked to the emitter-collector path of the transistor 57.

Furthermore, the resistors 56 and 60 and the emitters of the transistors 57 and 61 are connected in parallel to the terminals of the secondary windings S1 and S2 opposite those connected to the diodes 54 and 58.

Figure 5:
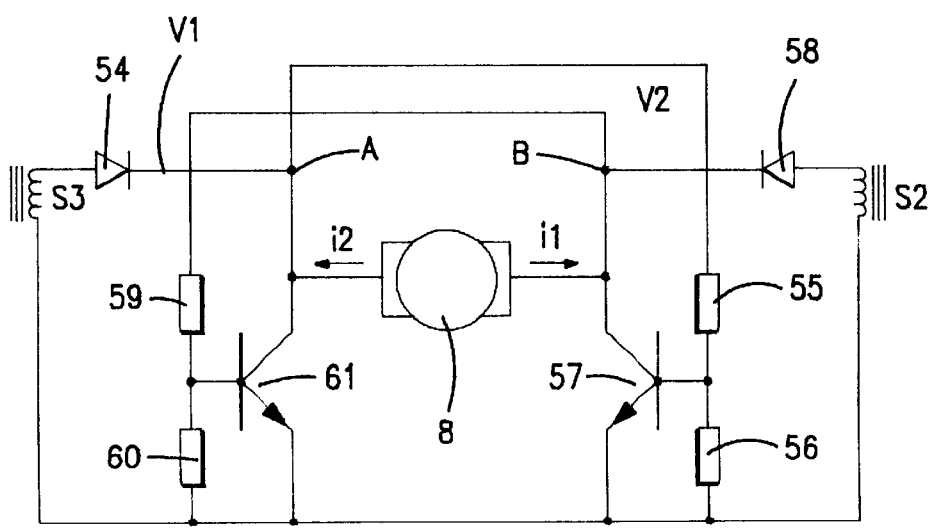
FIG. 5 is an electrical flow chart for the circuit controlling the power supply to the electric motor of the elongation device according to the invention.

The functioning of the arrangement described with reference to FIG. 5 is as follows.

It is first assumed that only the secondary winding S1 is being powered and consequently generating current. If S1 is generator, a rectified voltage V1 appears at the output of the diode 54 and, by virtue of the divider bridge consisting of the resistors 55 and 56, the transistor 57 is suitably polarized and thus becomes conductive. A current i1 can thus circulate in the motor 8 and initiate its rotation in one direction.

Likewise, when only the secondary winding S2 is generating, it is the transistor 61 which is made conductive as a result of the presence, on the voltage divider consisting of the resistors 59 and 60, of the output voltage V2 of the diode 58.

Thus, a current i2 with a direction counter to that of current i1 passes through the motor 8 and initiates its rotation in the opposite direction.

It will thus be seen that a circuit is in this way obtained which acts as a bridge rectifier in which the direction of the current is controlled by the voltages which appear at the terminals of one or other of the two secondary windings S1 and S2.

In the description of the circuit for powering the primary windings P1 and P2 which is represented in FIG. 3, it was indicated that the one primary winding P1 or P2 which is not intended to participate in powering the motor 8, in order to drive it in a defined direction, receives from the oscillator 40 a supply current for compensation of the diverted flux which passes through it and which is generated in the magnetic circuit 24b of the transformer 20 by the one of the primary windings P2 or P1 which is powered.

The first part 21 of the transformer 20 of the device according to the invention also has the function of transmitting counting pulses via the primary winding P3.

FIG. 6 represents the circuit which ensures that this function can be accomplished.

This circuit, which in FIG. 2 bears the general reference number 33, principally includes two diodes 64, 65 connected respectively to the points A and B of the circuit in FIG. 5 at which the rectified output voltages of the secondary windings Sl and S2 appear when these are powered. The cathodes of the diodes 64, 65 are connected together to a positive input of an operational amplifier 66 by way of a resistor 67 and on the other hand to a supply terminal of the operational amplifier 66. The negative terminal of the operational amplifier 66 is connected to the output of the position sensor 16.

Furthermore, a resistor 68 is connected between the positive input of the amplifier 66 and its output, another resistor 69 is connected between the negative input of the amplifier 66 and its output, while a capacitor 70 is connected between the negative input of the operational amplifier 66 and earth.

A resistor 71 is connected between the positive input of the amplifier 66 and earth.

The arrangement thus established forms a multivibrator whose output delivers to the primary winding P3.

Finally, the output of the operational amplifier 66 is connected to the primary winding P3, to which a capacitor 72 is connected in parallel.

The tuned circuit formed by the primary winding P3 and the capacitor 72 is tuned to a frequency equal to 170 kHz, which is the frequency of the multivibrator.

The operational amplifier 66 around which the multivibrator is formed is at all times powered at the same polarity whatever the direction of rotation of the motor 8 by virtue of the diodes 64 and 65.

The input of the multivibrator 66 is connected to the fixed contacts 73 of the incremental sensor 16 whereas its slide contact 74 is connected to electrical zero.

Thus, the normally blocked multivibrator delivers a pulse train each time the slide contact 74 is situated between two fixed contacts 73, that is to say three times per rotation of the threaded rod 13, 14 of the elongation device represented in FIG. 1.

Figure 4:
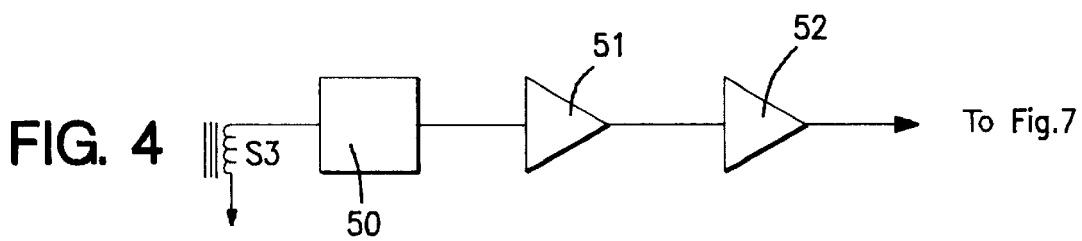
FIG. 4 is a block diagram of a circuit for filtering the output signals, indicating the state of elongation of the system.

The circuit represented in FIG. 7, which in FIG. 2 bears the reference number 34, is made up of a reversible counter 75 comprising a first input connected to the output of the shaping circuit 31 represented in FIG. 4, and of which a second input is connected to the output of the comparator 48 for determining the direction of rotation of the drive motor 8 linked to the inverter 47 of the power circuit in FIG. 3.

The reversible counter is in turn connected to a circuit for displaying the value and the direction of the movement of the extension 5 relative to the sleeve 4 of the intramedullary elongation device according to the invention.

The three principal functions of the said device according to the invention, namely the transmission of electrical energy through the patient's skin, the control of the direction of rotation of the motor for driving the elongation device, and the determination of the movement obtained, can be realized using one single transformer.

The electronic devices associated with this transformer make it possible at the same time to make the best use of the energy transmitted and to retransmit the information without these various functions interfering with each other.

It will thus be seen that by virtue of the arrangement which has just been described, the operations of elongation of a long bone such as the femur are performed in a perfectly controlled manner and that it is possible in particular to control the steps of the elongation which is to be obtained.

Furthermore, the device according to the invention permits permanent reading of the elongation values obtained.

Finally, the device according to the invention includes a part which is situated entirely within the body of the patient and can be controlled from the outside by simple contact with the skin, which fact obviates any passage through the flesh and skin and consequently eliminates the problems of sepsis.

We claim:
1. Elongation device for long bones, comprising an intramedullary nail which includes a tubular sleeve (4), an extension (5) which can slide axially inside the sleeve (4), the sleeve and the extension comprising means (6; 7) allowing them to be rigidly connected to two bone portions separated by an osteotomy, and means for moving the extension (5) relative to the sleeve (4) and capable of imparting to the intramedullary nail, and also to the bone intended to receive it, a gradual elongation, the means for moving the extension (5) relative to the sleeve (4) comprising an electric motor (8) which is arranged in the sleeve (4) and is linked to a speed reducer (9) for driving a screw/nut assembly (13, 14, 15) for moving the extension (5) relative to the sleeve, and means (2) for supplying power to the electric motor (8) and for automatically controlling the value and direction of the movement imparted to the extension (5) in the sleeve (4) by the screw/nut assembly (13, 14, 15) driven by the electric motor (8), the said power supply and control means including a transformer (20) which comprises a first part (21) intended to be implanted beneath the patient's skin and a second part (22) intended to be applied upon the patient's skin in line with the first part (21), wherein the first part (21) of the transformer includes a magnetic circuit (24a) having, on two end branches, secondary windings (S1, S2) for supplying power to the electric motor (8) in two opposite directions, and, on an intermediate branch (24c), a primary winding (P3) for receiving signals of the position of the screw (13, 14) of the screw/nut assembly (13, 14, 15), which signals come from a position sensor (16) driven by the reducer (9), while the second part (22) of the transformer (20) intended to be arranged in line with the first part by being applied against the patient's skin includes a magnetic circuit (24b) having, on two end branches, primary windings (P1, P2) connected to a supply circuit (30) and intended to cooperate with the secondary windings (S1, S2) of the first part (21) and, on an intermediate branch (24d), a secondary winding (S3) intended to cooperate with the primary winding (P3) of the first part (21) in order to transmit the position signals of the screw/nut assembly (13, 14, 15) to a filtering and shaping circuit (31).

2. Elongation device according to claim 1, wherein the screw/nut assembly of the intramedullary nail includes a rod (13) including a threaded portion (14) which cooperates with a skirt (15) forming a nut which prolongs the extension (5) inside the sleeve (4), the rod (13) with threaded portion (14) being connected to the output shaft (10) of the speed reducer (9).

3. Elongation device according to claim 2, wherein the rod (13) with threaded portion (14) is connected to the output shaft (10) of the reducer (9) by way of an axial damper (11).

4. Elongation device according to claim 2, wherein the rod (13) with threaded portion (14) drives the position sensor (16) made up of an incremental sensor of the position of the said rod (13) and consequently of the movement of the extension (5) relative to the sleeve (4).

5. Elongation device according to claim 1, wherein the intermediate branches (24c, 24d) of the magnetic circuits (24a, 24b) of the first and second parts (21, 22) of the transformer are arranged at unequal distances from the corresponding end branches of each of the said magnetic circuits, which ensures there can be no confusion of the position of the poles of the first part (21) relative to those of the second part (22) of the transformer (20).

6. Elongation device according to claim 1, wherein the supply circuit (30) of the primary windings (P1, P2) of the second part (22) of the transformer includes an oscillator (40) generating supply signals of a first frequency, the said oscillator being connected directly to a main power amplifier (41) and, by way of a divider (42, 43), to a compensation amplifier (44), the main power amplifier (41) and the compensation amplifier (44) being connected to the primary windings (P1, P2) by way of an inverter (47) intended to apply the output signal of the power amplifier (41) to one of the primary windings (P1, P2) to be supplied, and to apply the output signal of the compensation amplifier to the other primary winding (P2, P1) in which the effect of the diverted flux resulting from the supply of the said primary winding is to be compensated.

7. Elongation device according to claim 1, wherein the secondary winding (S3) carried by the magnetic circuit of the second part (22) of the transformer is connected to a circuit (50) for filtering the position signals of the screw/nut system (13, 14, 15), itself connected by way of a detector (51) to a shaping circuit (52).

8. Elongation device according to claim 1, additionally comprising a circuit (32) for determining the direction of rotation of the electric motor (8) for driving the screw/nut system (13, 14, 15), this circuit comprising two rectifier circuits (55, 58, 60, 61, 59, 54, 56, 57) which are connected respectively to the secondary windings (S1, S2) and whose conduction, initiated by the supply to one of these secondary windings, initiates the rotation of the motor in one direction or the other.

9. Elongation device according to claim 1, wherein the primary winding (P3) of the first part (21) of the transformer (20) is connected to a circuit (33) generating signals of the angular position of the nut/screw assembly (13, 14, 15), which includes the angular sensor (16) of the position of a threaded rod (13, 14) driven by the reducer (9), and whose outlet is connected to the negative input of an operational amplifier (66) whose positive input is connected by way of diodes (64, 65) of same polarity to points (A, B) of the circuit (30) for determining the direction of rotation of the electric motor (8) at which the rectified output voltage of each of the secondary windings (S1, S2) appears, the operational amplifier forming part of a multivibrator (66, 68, 69, 70, 71) which is connected to a tuned circuit formed by the primary winding (P3) and by a tuned capacitor (72) at a different frequency than that of the oscillator (40) of the supply circuit.

10. Elongation device according to claim 1, additionally including a circuit (34) for calculating and displaying the value and direction of the movement of the extension (5) relative to the sleeve (4), comprising a reversible counter (75) of which a first input is connected to the output of the circuit (31) for filtering and shaping of the position signals of the nut/screw assembly which are received by the secondary winding (S3) of the said second part (22) of the transformer, a second input of the reversible counter being connected to the output of a comparator (48) linked to the inverter (47) of the circuit (30) for supplying the primary windings (P1, P2) of the second part (22) of the transformer and intended to deliver a signal with two states corresponding respectively to the supply by the main power amplifier (41) of one or other of the primary windings (P1, P2) and a display circuit (76) connected to the output of the said reversible counter.

\* \* \* \* \*